(12) United States Patent
Kim

(10) Patent No.: US 11,486,832 B2
(45) Date of Patent: Nov. 1, 2022

(54) LATERAL FLOW DIAGNOSTIC TESTING APPARATUS

(71) Applicant: Pebble-i Inc., Anyang-si (KR)

(72) Inventor: Soohong Kim, Gwangju-si (KR)

(73) Assignee: Pebble-i Inc., Anyang-si (KR)

( * ) Notice: Subject to any disclaimer, the term of this patent is extended or adjusted under 35 U.S.C. 154(b) by 77 days.

(21) Appl. No.: 17/308,074

(22) Filed: May 5, 2021

(65) Prior Publication Data
US 2021/0349034 A1     Nov. 11, 2021

(30) Foreign Application Priority Data
May 7, 2020    (KR) ......................... 10-2020-0054749

(51) Int. Cl.
*G01N 21/78* (2006.01)
*G01N 21/85* (2006.01)

(52) U.S. Cl.
CPC ............. *G01N 21/78* (2013.01); *G01N 21/85* (2013.01); *G01N 2201/0231* (2013.01)

(58) Field of Classification Search
CPC ............... G01N 21/78; G01N 21/85; G01N 2201/0231; G01N 33/54391; G01N 33/54388; G01N 33/558; B01L 2200/16; B01L 2300/0825; B01L 2400/0406; B01L 3/502715; B01L 3/50273; B01L 3/502; A61B 5/1455; A61B 5/1491; A61B 5/150358; A61B 5/150755; A61B 2010/0006
See application file for complete search history.

(56) References Cited

U.S. PATENT DOCUMENTS

| 5,788,928 A | 8/1998 | Carey et al. |
| 2015/0119723 A1 | 4/2015 | Lee et al. |
| 2016/0187333 A1 | 6/2016 | Moll et al. |
| 2018/0117501 A1 * | 5/2018 | Nose ............... B01D 21/26 |

FOREIGN PATENT DOCUMENTS

| CN | 207502542 U | 6/2018 |
| KR | 10-2013-0126124 A | 11/2013 |
| KR | 10-1742958 B1 | 6/2017 |
| KR | 10-2019-0072475 A | 6/2019 |

OTHER PUBLICATIONS

Office action dated Jun. 30, 2021 from Korean Patent Office for Korean Application No. 10-2020-0054749.
European Search Report dated Sep. 24, 2021 from the European Patent Office for European Application No. 21172375.4.

* cited by examiner

*Primary Examiner* — Jennifer Wecker
*Assistant Examiner* — Alea N. Martin
(74) *Attorney, Agent, or Firm* — Insight Law Group, PLLC; Seung Lee

(57) ABSTRACT

A lateral flow diagnostic testing apparatus including a measurement assembly in which a cartridge is loaded and which is inclined with respect to a main body housing in a lateral flow direction of the cartridge is disclosed. The main body housing and the measurement assembly is rotatably hinge-coupled to adjust an inclination angle. The inclination of the measurement assembly is adjustable by an inclination driving unit. A vibration actuator can be further included on a cartridge loading surface. In addition, a heating unit fixed to face the cartridge can be further included.

12 Claims, 13 Drawing Sheets

LATERAL FLOW DIAGNOSTIC TESTING APPARATUS

CROSS-REFERENCE TO RELATED APPLICATION(S)

This application claims priority from Korean Patent Application No. 10-2020-0054749, filed on May 7, 2020, in the Korean Intellectual Property Office, the disclosure of which is incorporated herein by reference in its entirety.

BACKGROUND

1. Field

The following description relates to a medical diagnostic testing apparatus, and more particularly, to a technology relating to lateral flow in vitro diagnosis.

2. Description of Related Art

Immune-chromatography is a method of diagnostic testing for a disease using immune reactivity of antigen-antibody binding and is referred to as a lateral flow assay in a viewpoint of a measurement structure or is also referred to as a rapid-kit in a viewpoint of a diagnostic testing time which is shorter than a time of a gene amplification test or the like.

In the general immune-chromatography, antibodies that are specifically bound to disease-causing antigens are bound to gold nanoparticles and immobilized on the conjugate pad, the other type of antibodies are immobilized on a porous membrane, and a specimen to be tested is absorbed by a sample pad and proceeds along the porous membrane. In a case in which the antigens are present in the specimen, the antigens bound to the gold nanoparticles of the conjugate pad are bound and move through the porous membrane to be bound to the antibodies immobilized on a test line, and thus a color of the gold nanoparticles is displayed along the test line to indicate a positive test result. In addition, the antibodies that are not bound to the antigens are bound at a control line, and thus a color of the gold nanoparticles is displayed along the control line.

In the conventional lateral flow rapid diagnostic tests, a test strip accommodated in a plastic cartridge is loaded on a flat surface, a specimen is input to the plastic cartridge, and a line is read visually after a time of about 5 to 15 minutes has elapsed. Recently, quantification or automation of diagnostic testing apparatuses may also be carried out using image sensors or photodiodes in order to reduce decision errors. In most such diagnostic testing apparatuses, since a reaction proceeds based on the capillary phenomenon, it takes a long time to diagnose.

SUMMARY

The proposed invention is directed to increasing reactivity in a lateral flow diagnostic testing apparatus to increase sensitivity thereof. The proposed invention is directed to increasing the reactivity in the lateral flow diagnostic testing apparatus to reduce a time taken for measuring.

In addition, the proposed invention is directed to increasing the reactivity in the lateral flow diagnostic testing apparatus to increase the sensitivity thereof. The proposed invention is directed to increasing the reactivity in the lateral flow diagnostic testing apparatus to reduce the time taken for measuring.

In one aspect, a structure which is inclined in a lateral flow direction of a cartridge to facilitate control of a lateral flow after a specimen is input is proposed.

According to an additional aspect, a structure in which an inclination angle of the cartridge may be controlled to adjust a speed of the flow when the specimen is input and mixed and flows in the lateral flow direction is proposed According to an additional aspect, a heating unit may be provided in the cartridge to adjust a temperature of the cartridge to an optimal reaction temperature.

In addition, a physical vibration unit is provided so that energy may be supplied from the outside to facilitate a reaction between a specimen and a reagent. In addition, vibration directions may also be individually controlled to facilitate a lateral flow and mixing.

Figure 1:
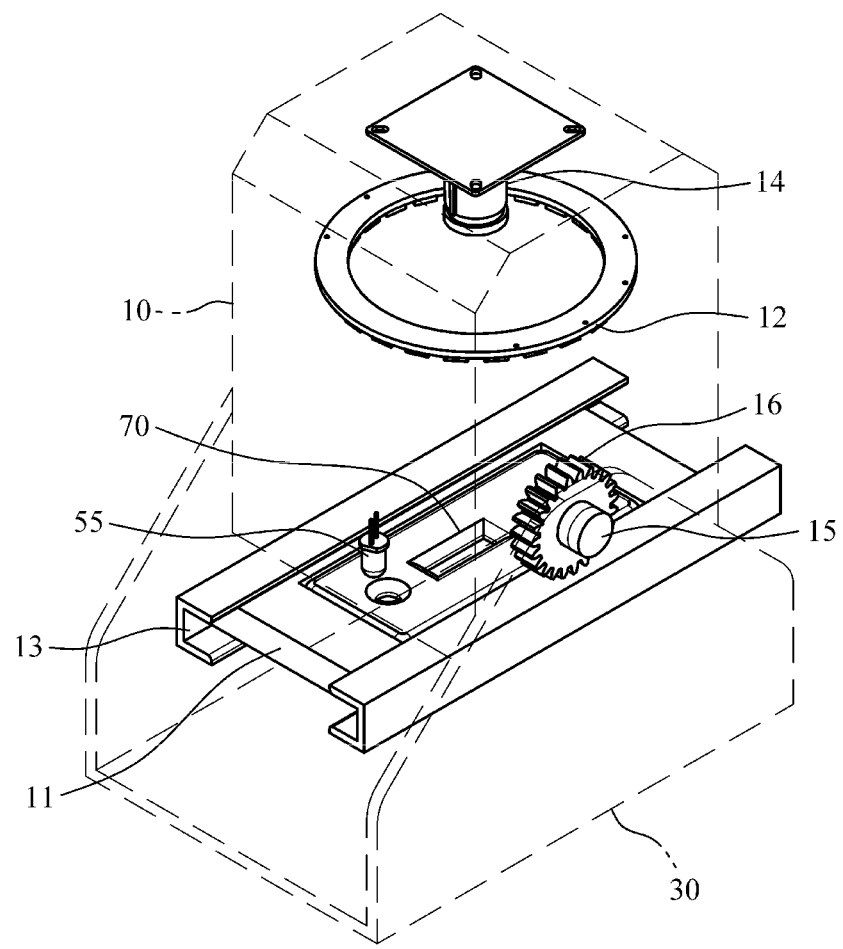
FIG. 1 is a three-dimensional perspective view illustrating a mechanical configuration of a lateral flow diagnostic testing apparatus according to one embodiment of the proposed invention.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Hereinafter, in order to facilitate understanding and reproduction of the proposed invention by those skilled in the art, the proposed invention will be described in detail.

FIG. 1 is a three-dimensional perspective view illustrating a mechanical configuration of a lateral flow diagnostic testing apparatus according to one embodiment of the proposed invention. As illustrated in the drawing, the lateral flow diagnostic testing apparatus according to one embodiment includes a main body housing 30 and a measurement assembly 10. According to one aspect, the measurement assembly 10 is inclined in a lateral flow direction of a cartridge with respect to the main body housing 30.

The measurement assembly 10 includes a cartridge loading surface, on which a cartridge 70 is loaded, and an accommodation groove, in which the lateral flow diagnosis cartridge 70 is loaded, is formed in the loading surface. In FIG. 1, an appearance of the cartridge 70 loaded in the accommodation groove is illustrated.

According to an additional aspect, the main body housing 30 and the measurement assembly 10 may be rotatably hinge-coupled. In the illustrated embodiment, the main body housing 30 includes an accommodation space in a lower portion, and the measurement assembly 10 rotates like a swing in the accommodation space of the main body housing 30 about the hinge unit 15. In one embodiment, an inclination angle formed by the measurement assembly 10 with respect to the main body housing 30 may be manually adjusted. By adjusting the inclination angle, a flow due to a capillary phenomenon of a specimen, catalyst, or reaction-related liquid in the lateral flow diagnosis cartridge 70 may be accelerated or decelerated.

According to an additional aspect, the inclination angle formed by the measurement assembly 10 with respect to the main body housing 30 may be adjusted in an automatic driving manner. In the illustrated embodiment, the lateral flow diagnostic testing apparatus may further include a hinge unit 15, an inclination driving unit 16, and a control unit 100. The hinge unit 15 rotatably couples the main body housing 30 and the measurement assembly 10. The inclination driving unit 16 is coupled to the hinge unit 15 to rotatably drive the measurement assembly 10 with respect to the main body housing 30. In one embodiment, the inclination driving unit 16 may be formed to include a rotary motor and selectively include one gear or a plurality of gears. In the illustrated embodiment, the motor is installed at the measurement assembly 10 to rotatably drive the main body housing 30 so as to adjust relative inclination. However, the present invention is not limited thereto, and the motor may also be installed at the main body housing 30 to rotatably drive the measurement assembly 10.

Figure 2:
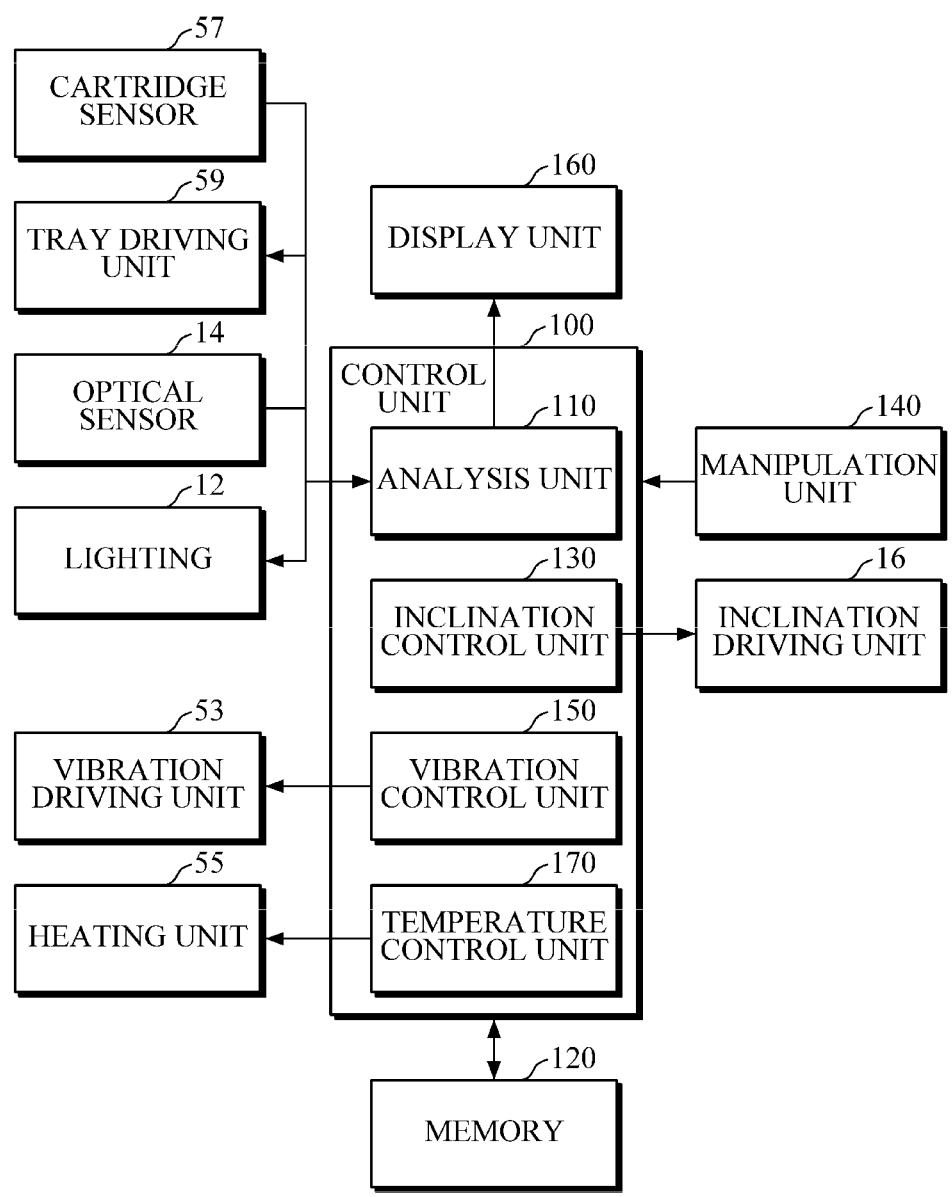
FIG. 2 is a block diagram illustrating a functional configuration of the lateral flow diagnostic testing apparatus according to one embodiment of the proposed invention.

FIG. 2 is a block diagram illustrating a functional configuration of the lateral flow diagnostic testing apparatus according to one embodiment of the proposed invention. In the embodiment illustrated in FIG. 1, the control unit 100 is implemented on a substrate fixed to a lateral side of the measurement assembly 10 to include a microprocessor. In the embodiment illustrated in FIG. 2, an analysis unit 110, an inclination control unit 130, a vibration control unit 150, and a temperature control unit 170, which are illustrated as components of the control unit 100, may be implemented as a program command set executed by the microprocessor. The program commands are stored and executed in a memory 120. The memory 120 may include one memory element or a plurality of different types of memory elements.

Referring to FIG. 2, in one embodiment, a manipulation unit 140 is implemented as a key button and includes a loading button for loading the cartridge 70. A display unit 160 displays information on an apparatus operation status, a user interface, a measurement value, and the like.

According to one aspect, the control unit 100 includes the inclination control unit 130. The inclination control unit 130 controls rotational driving of the inclination driving unit 16 to adjust inclination of the measurement assembly 10 with respect to the main body housing 30.

Figure 3:
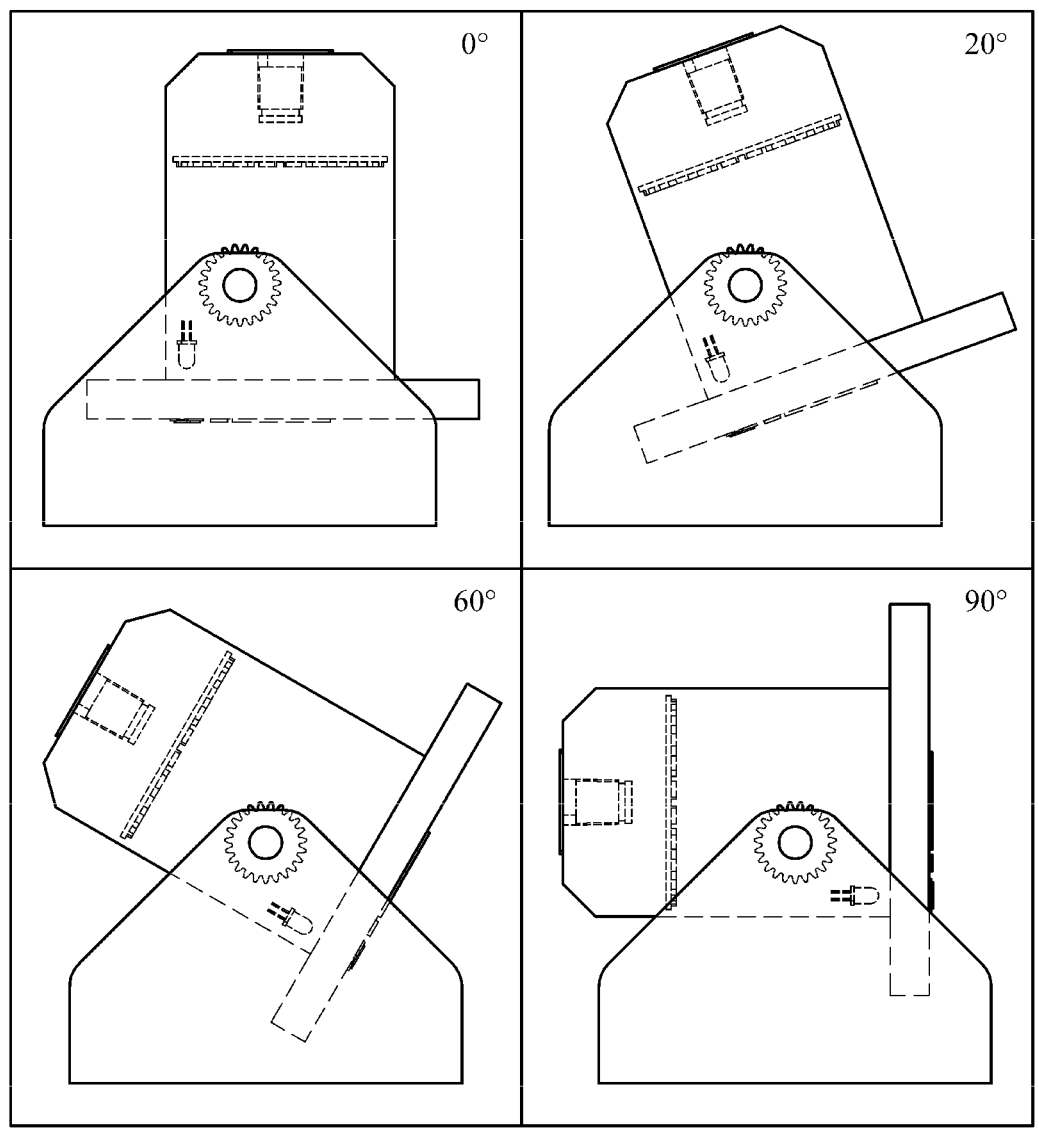
FIG. 3 is a set of views illustrating appearances of a measurement instrument illustrated in FIGS. 1 and 2 being driven to be inclined at angles.

FIG. 3 is a set of views illustrating appearances of a measurement instrument illustrated in FIGS. 1 and 2 being driven to be inclined at angles. An angle of 0° is an angular position when the cartridge 70 is loaded on a tray. In FIG. 3, cases in which angles formed between the measurement assembly 10 and the main body housing 30 are 20°, 60°, and 90° are additionally illustrated. In a case in which inclination is formed in the lateral flow direction so that a side of a sample pad in the cartridge to which a specimen is input is higher, a lateral flow may be accelerated. The inclination control unit 130 of the control unit 100 may change an inclination angle according to a type of the cartridge 70 and an operation of measurement.

According to one aspect, the measurement assembly 10 may include a tray 11 on which the cartridge 70 is loaded. The accommodation groove in which the lateral flow diagnosis cartridge 70 is accommodated and fixed is formed in an upper surface of the tray 11. In the illustrated embodiment, the tray 11 is slidably coupled to the measurement assembly 10. In the illustrated embodiment, the tray 11 is guided by a tray rail 13 to be withdrawn in a forward direction, the cartridge 70 is loaded on the tray 11, and then the tray 11 returns to a measurement position.

In the illustrated embodiment, a cartridge sensor 57 configured to detect whether the cartridge 70 is loaded is provided above the upper surface of the tray 11. In one embodiment, the cartridge sensor 57 is installed above a cartridge accommodation groove and formed as a light sensor configured to detect the cartridge. In addition, in the illustrated embodiment, a tray driving unit 59 configured to withdraw and return the tray 11 along the tray rail 13 is provided. The tray driving unit 59 may be implemented to include a rack structure formed at a side surface of the tray, a motor, and a pinion gear fixed to a rotary shaft thereof.

Figure 4:
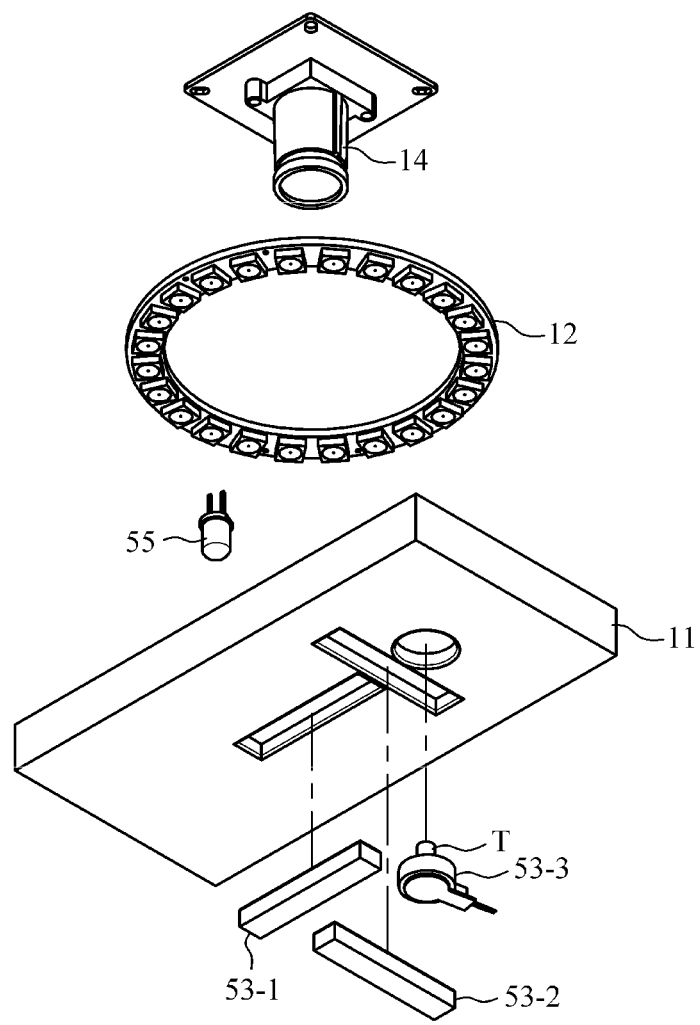
FIG. 4 is an exploded perspective view illustrating main parts of the embodiment illustrated in FIG. 1.

According to an additional aspect, the measurement assembly 10 may further include an optical sensor 14. In the illustrated embodiment, the optical sensor 14 is fixed to a ceiling surface of the measurement assembly 10 above the tray 11. FIG. 4 is an exploded perspective view illustrating main parts of the embodiment illustrated in FIG. 1. In the embodiment illustrated in FIGS. 1 and 4, the optical sensor 14 is implemented as a camera module. However, the optical sensor 14 is not limited thereto and may also be provided as a light detecting element. In addition, the measurement assembly 10 may further include lighting 12. The lighting 12 is carefully arranged above the loading surface of the tray 11 on which the cartridge 70 is loaded to provide sufficient and uniform light in order to not miss a weak color reaction.

Referring to FIG. 2 again, in the illustrated embodiment, the control unit 100 may include the analysis unit 110. The analysis unit 110 analyzes an image input from the optical sensor 14 to determine a color of the cartridge 70 so as to process a diagnosis. From the image obtained from the optical sensor 14, that is, the camera, a color development portion around a test line and a control line may be detected on the basis of a luminance value.

According to an additional aspect, a reaction between the specimen and a reagent may be facilitated by vibrating the cartridge 70 to supply energy from the outside. In one embodiment, the measurement assembly 10 may further include a vibration driving unit 53. The vibration driving unit 53 provides mechanical vibration to facilitate a reaction of a specimen, catalyst, or reaction-related liquid in the lateral flow cartridge 70. For example, among a linear resonant actuator (LRA), an eccentric rotating mass (ERM), and a piezo transducer or ultrasonic transducer, one actuator or a plurality of actuators may be selected as the vibration driving unit 53. In addition, the vibration driving unit 53 may be driven in a manner that obtains vibration by rapidly moving the tray driving unit 59 or a tray conveying motor back and forth.

As illustrated in FIG. 4, which is the exploded perspective view illustrating the main parts of the embodiment illustrated in FIG. 1, the vibration driving unit 53 may include an X-axis vibration unit 53-1. In the illustrated embodiment, the X-axis vibration unit 53-1 vibrates the cartridge 70 in a longitudinal direction, that is, the lateral flow direction. In one embodiment, the X-axis vibration unit 53-1 is implemented as the LRA installed in an X-axis direction.

In addition, the vibration driving unit 53 may further include a Y-axis vibration unit 53-2. The Y-axis vibration unit 53-2 vibrates the cartridge 70 in a width direction. Such vibration in the width direction may supply energy to facilitate a biochemical reaction. In the illustrated embodiment, the Y-axis vibration unit 53-2 is implemented as the LRA installed in a Y-axis direction.

In addition, the vibration driving unit 53 may further include a Z-axis vibration unit 53-3. The Z-axis vibration unit 53-3 vibrates the cartridge 70 in a thickness direction. In the illustrated embodiment, the Z-axis vibration unit 53-3 is implemented as the LRA installed in a Z-axis direction. The X-axis vibration unit 53-1, the Y-axis vibration unit 53-2, and the Z-axis vibration unit 53-3 may be driven in a manner that obtains vibration by moving the tray driving unit 59 or a tray conveying motor back and forth.

Figure 5:
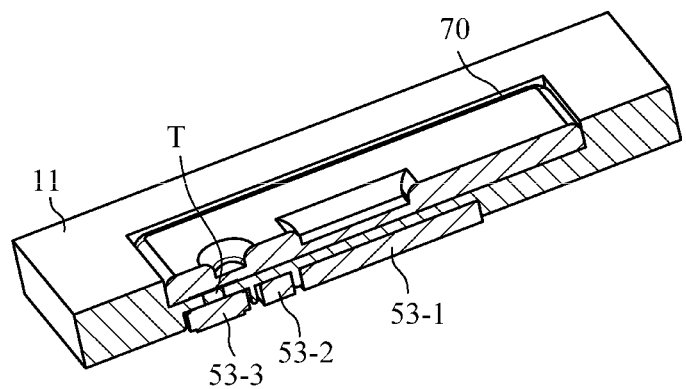
FIG. 5 is a cross-sectional view illustrating a configuration of both of a tray and a cassette loaded thereon according to one embodiment.

FIG. 5 is a cross-sectional view illustrating a configuration of both of a tray and a cassette loaded thereon according to one embodiment. In the illustrated embodiment, the X-axis vibration unit 53-1, the Y-axis vibration unit 53-2, and the Z-axis vibration unit 53-3 are embedded in the tray 11 and vibrate the tray in the directions. However, the proposed invention is not limited thereto. For example, the accommodation groove may be formed in the tray 11 as a separate container in which the cartridge 70 is loaded, and the separate container may also be coupled thereto using the remaining portion of the tray 11, the X-axis vibration unit 53-1 and the Y-axis vibration unit 53-2.

According to an additional aspect, the Z-axis vibration unit 53-3 may include an oscillator tip exposed to be in direct contact with the cartridge through a hole in a bottom of the loading surface on which the cartridge is loaded. In the embodiment illustrated in FIG. 5, an oscillator tip T may be in direct contact with the cartridge 70 through the hole in the bottom of the tray 11. In this case, the hole is formed in a bottom of a cartridge accommodation groove of the tray 11. A housing of the Z-axis vibration unit 53-3 is fixed to a fixing groove of the bottom surface of the tray, and the oscillator tip T may be exposed to protrude through the hole in the bottom of the cartridge accommodation groove of the tray 11. In one embodiment, the oscillator tip has a circular shape and provides vibration in the Z-axis direction to an end side of the cartridge in the lateral flow direction. In the illustrated embodiment, one oscillator tip is provided, but the oscillator tip is not limited thereto and may be provided as a plurality of oscillator tips.

According to an additional aspect, the lateral flow diagnostic testing apparatus may heat the cartridge 70 at a temperature sufficient for facilitating a reaction in the cartridge 70. In the illustrated embodiment, the lateral flow diagnostic testing apparatus may further include a heating unit 55. The heating unit 55 may be fixed to the measurement assembly to face the cartridge 70. In one embodiment, the heating unit 55 may be a heating wire arranged on the bottom or outer side surface of the accommodation groove, in which the cartridge is accommodated, of the tray.

According to an additional aspect, the heating unit 55 may be a non-contact type infrared heater. As illustrated in FIGS. 1, 2, and 4, the infrared heater 55 is installed in the measurement assembly 10 to face the cartridge 70 from above the tray so as to heat around the test line of the cartridge 70.

Figure 6:
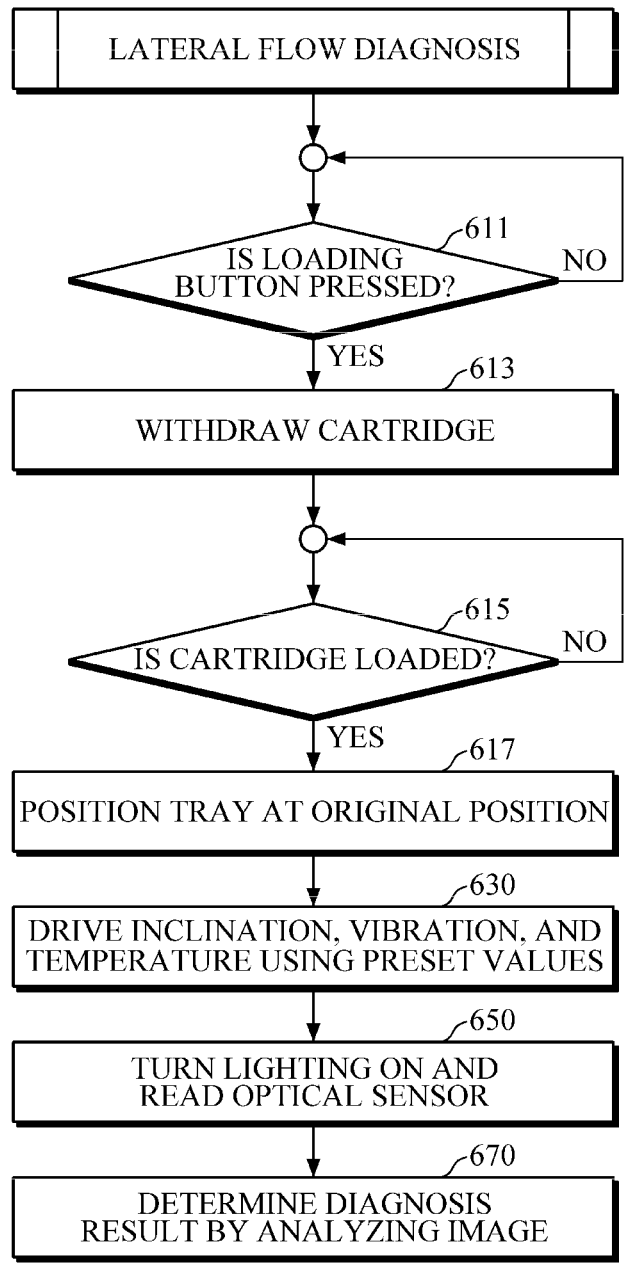
FIG. 6 is a flowchart illustrating operations of a lateral flow in vitro diagnosis method according to one embodiment of the proposed invention.

FIG. 6 is a flowchart illustrating operations of a lateral flow in vitro diagnosis method according to one embodiment of the proposed invention. The method of FIG. 6 will be described with reference to the block diagram of FIG. 2. As illustrated in the drawing, the analysis unit 110 of the control unit 100 detects that the loading button on the manipulation unit 140 is pressed to start an analysis treatment. The analysis unit 110 drives the tray driving unit 59 to withdraw the tray 11. Then, when it is detected that the cartridge 70 is loaded on the tray 11 through the cartridge sensor 57, the tray driving unit 59 is driven to pull the tray 11 to an original position. Then, the inclination driving unit 16 is driven to have predetermined inclination through the inclination control unit 130, the vibration driving unit 53 is driven through the vibration control unit 150 in one preset direction or the plurality of preset directions, and the heating unit 55 is driven to heat at a preset optimal temperature through the temperature control unit 170. Then, the analysis unit 110 turns the lighting 12 on, captures an image using the optical sensor 14, analyzes the captured image to detect a color development of the test line and a color development of the control line so as to process a diagnosis, and outputs a result thereof to the display unit 160.

Figure 7:
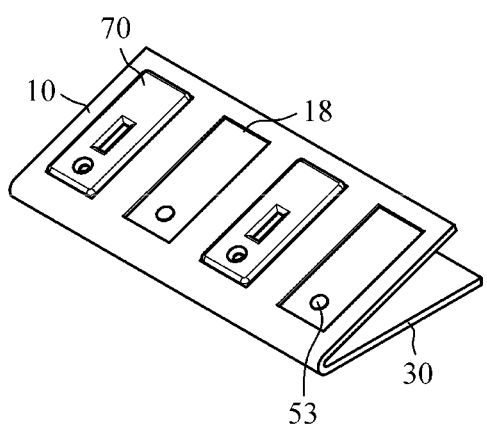
FIG. 7 is a view illustrating an exterior of a lateral flow diagnostic testing apparatus according to another embodiment.

FIG. 7 is a view illustrating an exterior of a lateral flow diagnostic testing apparatus according to another embodiment. As illustrated in the drawing, a lateral flow diagnostic testing apparatus according to one embodiment includes a main body housing 30 and a measurement assembly 10. According to one aspect, the measurement assembly 10 is inclined with respect to the main body housing 30 in a lateral flow direction of a cartridge. In the illustrated embodiment, the main body housing 30 and the measurement assembly 10 have an integral structure having a plate shape in which corners are connected, but the proposed invention is not limited thereto, and for example, the main body housing 30 and the measurement assembly 10 may be provided as a polyhedron having a triangular pyramid shape.

The measurement assembly 10 includes a cartridge loading surface, on which cartridges 70 are loaded, and accommodation grooves 18, in which the lateral flow diagnosis cartridges 70 are loaded, are formed on the loading surface. In the embodiment of FIG. 7, the measurement assembly 10 includes four accommodation grooves 18 so that up to four cartridges may be used at the same time. In the diagnostic testing apparatus, the cartridges 70 are loaded in first and third accommodation grooves 18, and the second and fourth accommodation grooves 18 are empty.

Unlike the embodiment illustrated in FIGS. 1 to 3, in the embodiment of FIG. 7, an inclination angle formed by the measurement assembly 10 with respect to the main body housing 30 is fixed. For example, a structure may be implemented in which the inclination angle formed between the measurement assembly 10 and the main body housing 30 is manually adjusted using a hinge and a fixing end.

According to an additional aspect, reactivity between a specimen and a reagent may be facilitated by vibrating the cartridge 70 to supply energy from the outside. In the embodiment illustrated in FIG. 7, the measurement assembly 10 may further include a vibration driving unit 53. The vibration driving unit 53 provides mechanical vibration in order to facilitate a reaction of a specimen, catalyst, or reaction-related liquid in the lateral flow cartridge 70. For example, among an LRA, an ERM, and a piezo transducer or ultrasonic transducer, one actuator or a plurality of actuators may be selected as the vibration driving unit 53. In addition, the vibration driving unit 53 may be driven in a manner that obtains vibration by rapidly moving the tray driving unit 59 or a tray conveying motor back and forth.

Figure 8:
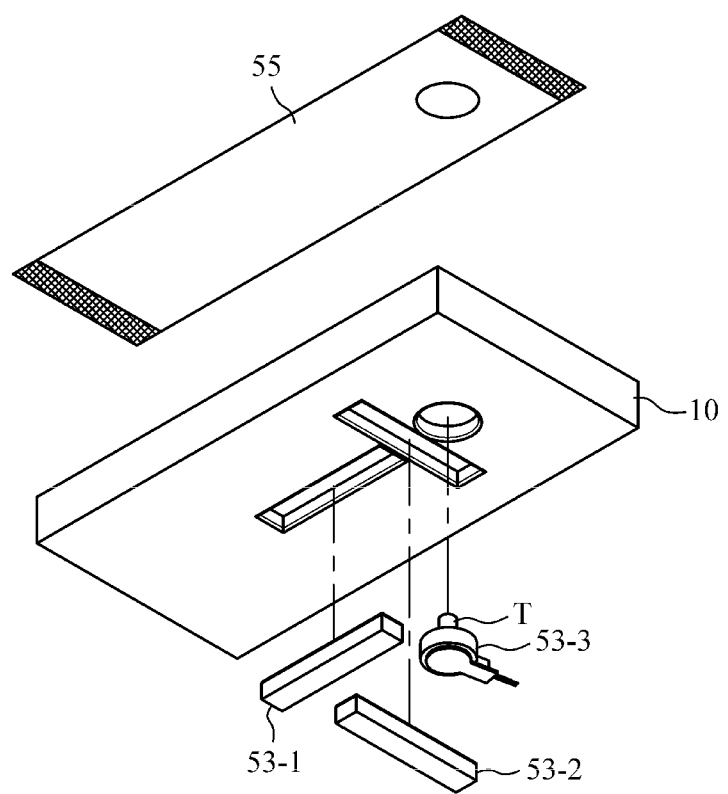
FIG. 8 is an exploded perspective view illustrating main parts of the embodiment illustrated in FIG. 7.

FIG. 8 is an exploded perspective view illustrating main parts of the embodiment illustrated in FIG. 7. As illustrated in the drawing, the vibration driving unit 53 may include an X-axis vibration unit 53-1. In the illustrated embodiment, the X-axis vibration unit 53-1 vibrates the cartridge 70 in a longitudinal direction, that is, the lateral flow direction. In one embodiment, the X-axis vibration unit 53-1 is implemented as the LRA installed in an X-axis direction.

In addition, the vibration driving unit 53 may further include a Y-axis vibration unit 53-2. The Y-axis vibration unit 53-2 vibrates the cartridge 70 in a width direction. Such vibration in the width direction may supply energy to facilitate a biochemical reaction. In the illustrated embodiment, the Y-axis vibration unit 53-2 is implemented as the LRA installed in a Y-axis direction.

In addition, the vibration driving unit 53 may further include a Z-axis vibration unit 53-3. The Z-axis vibration unit 53-3 vibrates the cartridge 70 in a thickness direction. In the illustrated embodiment, the Z-axis vibration unit 53-3 is implemented as the LRA installed in a Z-axis direction. The X-axis vibration unit 53-1, the Y-axis vibration unit 53-2, and the Z-axis vibration unit 53-3 may be driven in a manner that obtains vibration by moving the tray driving unit 59 or a tray conveying motor back and forth.

Similarly to the embodiment described above with reference FIG. 5, the X-axis vibration unit 53-1, the Y-axis vibration unit 53-2, and Z-axis vibration unit 53-3 are embedded in a lower portion of the measurement assembly 10 to vibrate the cartridge in the directions. However, the proposed invention is not limited thereto. For example, in the measurement assembly 10, the accommodation groove in which the cartridge 70 is loaded may be provided as a separated container, and the separate container may also be coupled thereto using the remaining portion of the measurement assembly 10, the X-axis vibration unit 53-1 and the Y-axis vibration unit 53-2.

According to an additional aspect, the Z-axis vibration unit 53-3 may include an oscillator tip exposed to be in direct contact with the cartridge through a hole in a bottom of the loading surface on which the cartridge is loaded. In the embodiment illustrated in FIGS. 7 and 8, an oscillator tip T may be in direct contact with the cartridge 70 through a hole in a bottom of the measurement assembly 10. In this case, the hole is formed in a bottom of the accommodation groove of the measurement assembly 10. A housing of the Z-axis vibration unit 53-3 is fixed to a bottom surface fixing groove of the measurement assembly 10, and the oscillator tip T may protrude and be exposed through the hole in the bottom of the cartridge accommodation groove of the measurement assembly 10. In one embodiment, the oscillator tip has a circular shape and provides vibration in the Z-axis direction to an end side of the cartridge in the lateral flow direction. In the illustrated embodiment, one oscillator tip is provided, but the oscillator tip is not limited thereto and may be provided as a plurality of oscillator tips.

According to an additional aspect, the lateral flow diagnostic testing apparatus may heat the cartridge 70 at a temperature sufficient for facilitating a reaction in the cartridge 70. In the illustrated embodiment, the lateral flow diagnostic testing apparatus may further include a heating unit 55. The heating unit 55 may be fixed to the measurement assembly to face the cartridge 70. In the illustrated embodiment, the heating unit 55 may be implemented as a heating wire arranged in a bottom surface of the accommodation groove in which the cartridge of a tray 11 is accommodated.

Figure 9:
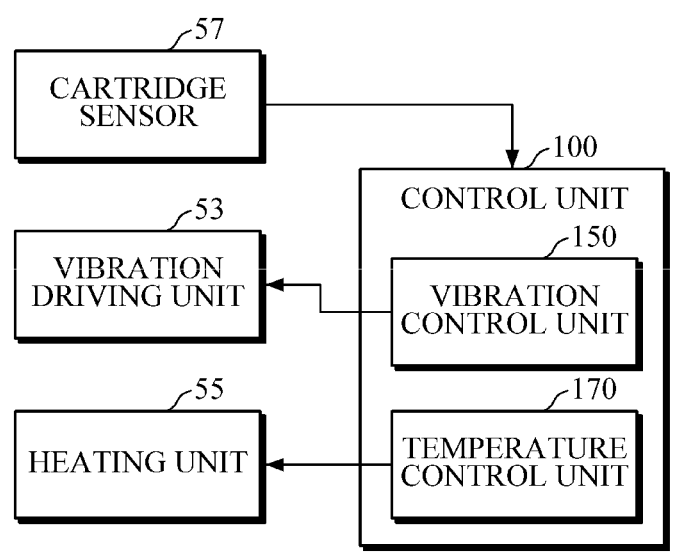
FIG. 9 is a block diagram illustrating a functional configuration of the lateral flow diagnostic testing apparatus according to the embodiment illustrated in FIG. 7.

FIG. 9 is a block diagram illustrating a functional configuration of the lateral flow diagnostic testing apparatus according to the embodiment illustrated in FIG. 7. In the embodiment illustrated in FIG. 7, the control unit 100 is implemented on a substrate fixed to the bottom of the measurement assembly 10 as an electrical circuit including a logic circuit. In the embodiment illustrated in FIG. 9, a configuration of a vibration control unit 150 and a temperature control unit 170 provided as a configuration of the control unit 100 may be implemented as the electrical circuit including the logic circuit. In the illustrated embodiment, a cartridge sensor 57 configured to detect whether the cartridge 70 is loaded is provided above an upper surface of the tray 11. In one embodiment, the cartridge sensor 57 is implemented as a light sensor installed above the cartridge accommodation groove to detect the cartridge.

When a power source is turned on, the control unit 100 intermittently activates the cartridge sensor 57 to check whether the cartridge 70 is loaded on the tray 11. When the cartridge is detected at one of four accommodation grooves, the vibration driving unit 53 is driven in one direction or the plurality of directions through a corresponding vibration control unit 150, and the heating unit 55 is driven to heat at an optimal temperature through the temperature control unit 170. A user may visually check a diagnosis result by checking a test line and a control line.

Figure 10:
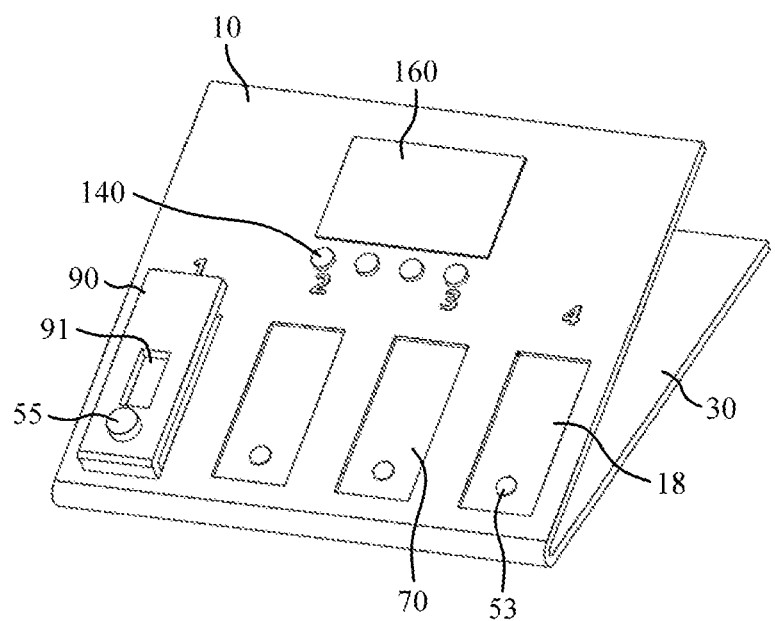
FIG. 10 is a view illustrating an exterior of a lateral flow diagnostic testing apparatus according to still another embodiment of the proposed invention.

FIG. 10 is a view illustrating an exterior of a lateral flow diagnostic testing apparatus according to still another embodiment of the proposed invention. As illustrated in the drawing, a lateral flow diagnostic testing apparatus according to one embodiment includes a main body housing 30 and a measurement assembly 10. According to one aspect, the measurement assembly 10 is inclined in a lateral flow direction of a cartridge with respect to the main body housing 30. In the illustrated embodiment, the main body housing 30 and the measurement assembly 10 have an integrated structure having a plate shape of which corners are connected, but the proposed invention is not limited thereto, and for example, the main body housing 30 and the measurement assembly 10 may be provided as a polyhedron having a triangular pyramid shape.

The measurement assembly 10 includes a cartridge loading surface, on which cartridges 70 are loaded, and accommodation grooves 18, in which the lateral flow diagnosis cartridges 70 are loaded, are formed on the loading surface. In the embodiment of FIG. 10, the measurement assembly 10 includes four accommodation grooves 18 so that up to four cartridges may be used at the same time. In order to describe the present invention, FIG. 10 shows a complete exterior of a first accommodation groove, appearances of second and fourth accommodation grooves in which clamps 90 are removed in a state in which the cartridges are not loaded, and an appearance of a third accommodation groove in which the clamp 90 is removed in a state in which the cartridge is loaded.

Similarly to the embodiment of FIG. 7, in the embodiment of FIG. 10, an inclination angle formed by the measurement assembly 10 with respect to the main body housing 30 is fixed. However, in such a structure, for example, the measurement assembly 10 and the main body housing 30 may be easily changed into a structure in which the inclination angle is manually adjusted using a hinge and a fixing end.

According to an additional aspect, the measurement assembly 10 may further include the clamp 90 pressing and pressurizing the cartridge from above. In the embodiment illustrated in FIGS. 10 and 11, a configuration of the clamp 90 will be described in more detail. The clamp 90 is coupled to an upper surface of the measurement assembly 10 to be rotatable through a hinge 95. After a sample is input to the cartridge, when the clamp is opened and the cartridge is installed on the clamp, and a measurement start button presses, a measurement process is started.

In the illustrated embodiment, since elastic rubber 97 is attached to an inner lower surface of the clamp 90, when the clamp is coupled thereto, an upper surface of the loaded cartridge is pressed, and thus vibration of a vibration driving unit is smoothly transmitted to the cartridge. In the illustrated embodiment, as a magnet 93 is provided at one end of the clamp, the clamp 90 is coupled to the upper surface of the measurement assembly 10. A user may check a measurement result through an observation window 91 in the upper surface of the clamp.

Lighting 12 may be further included around the observation window 91 inside the clamp 90. In order to not miss a weak color development reaction, the lighting 12 is carefully arranged above the loading surface, on which the cartridge 70 is loaded, to supply sufficient and uniform light.

According to an additional aspect, reactivity between a specimen and a reagent may be facilitated by vibrating the cartridge 70 to supply energy from the outside. In the embodiment illustrated in FIG. 10, the measurement assembly 10 may further include a vibration driving unit 53. The vibration driving unit 53 provides mechanical vibration in order to facilitate a reaction of a specimen, catalyst, or reaction-related liquid in the lateral flow cartridge 70. For example, among an LRA, an ERM, and a piezo transducer or ultrasonic transducer, one actuator or a plurality of actuators may be selected as the vibration driving unit 53. In addition, the vibration driving unit 53 may be driven in a manner that obtains vibration by rapidly moving the tray driving unit 59 or a tray conveying motor back and forth.

Figure 12:
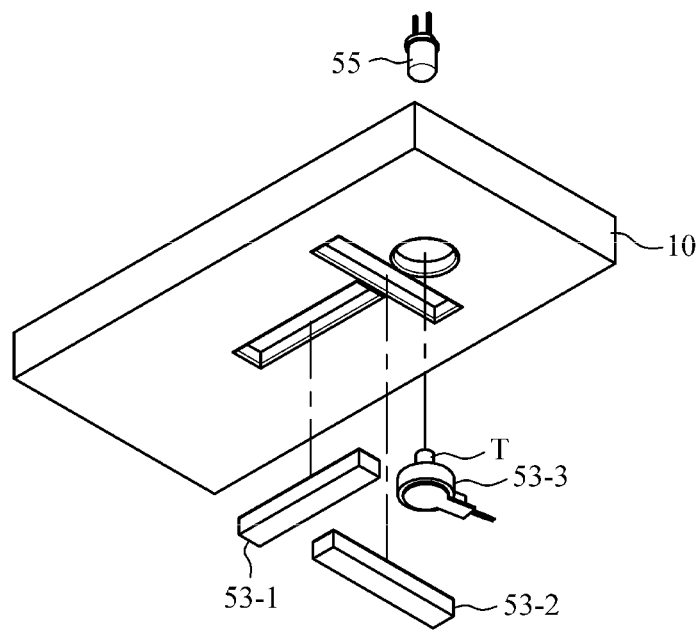
FIG. 12 is an exploded perspective view illustrating main parts of the embodiment of FIG. 10.

FIG. 12 is an exploded perspective view illustrating main parts of the embodiment of FIG. 10. As illustrated in the drawing, the vibration driving unit 53 may include an X-axis vibration unit 53-1. In the illustrated embodiment, the X-axis vibration unit 53-1 vibrates the cartridge 70 in a longitudinal direction, that is, the lateral flow direction. In one embodiment, the X-axis vibration unit 53-1 is implemented as the LRA installed in an X-axis direction.

In addition, the vibration driving unit 53 may further include a Y-axis vibration unit 53-2. The Y-axis vibration unit 53-2 vibrates the cartridge 70 in a width direction. Such vibration in the width direction may supply energy to facilitate a biochemical reaction. In the illustrated embodiment, the Y-axis vibration unit 53-2 is implemented as the LRA installed in a Y-axis direction.

In addition, the vibration driving unit 53 may further include a Z-axis vibration unit 53-3. The Z-axis vibration unit 53-3 vibrates the cartridge 70 in a thickness direction. In the illustrated embodiment, the Z-axis vibration unit 53-3 is implemented as the LRA installed in a Z-axis direction. The X-axis vibration unit 53-1, the Y-axis vibration unit 53-2, and the Z-axis vibration unit 53-3 may be driven in a manner that obtains vibration by moving the tray driving unit 59 or a tray conveying motor back and forth.

Similarly to the embodiment described above with reference to FIG. 5, the X-axis vibration unit 53-1, the Y-axis vibration unit 53-2, and Z-axis vibration unit 53-3 are embedded in a lower portion of the measurement assembly 10 to vibrate the cartridge in the directions. However, the proposed invention is not limited thereto. For example, in the measurement assembly 10, the accommodation groove in which the cartridge 70 is loaded may be provided as a separated container, and the separate container may also be coupled thereto using the remaining portion of the measurement assembly 10, the X-axis vibration unit 53-1 and the Y-axis vibration unit 53-2.

According to an additional aspect, the Z-axis vibration unit 53-3 may include an oscillator tip exposed to be in direct contact with the cartridge through a hole in a bottom of the loading surface on which the cartridge is loaded. In the embodiment illustrated in FIGS. 10 and 11, an oscillator tip T may be in direct contact with the cartridge 70 through a hole in a bottom of the measurement assembly 10. In this case, the hole is formed in a bottom of the accommodation groove of the measurement assembly 10. A housing of the Z-axis vibration unit 53-3 is fixed to a bottom surface fixing groove of the measurement assembly 10, and the oscillator tip T may protrude and be exposed through the hole in the bottom of the cartridge accommodation groove of the measurement assembly 10. In one embodiment, the oscillator tip has a circular shape and provides vibration in the Z-axis direction to an end side of the cartridge in the lateral flow direction. In the illustrated embodiment, one oscillator tip is provided, but the oscillator tip is not limited thereto and may be provided as a plurality of oscillator tips.

According to an additional aspect, the lateral flow diagnostic testing apparatus may heat the cartridge 70 at a temperature sufficient for facilitating a reaction in the cartridge 70. In the illustrated embodiment, the lateral flow diagnostic testing apparatus may further include a heating unit 55. The heating unit 55 may be fixed to the measurement assembly to face the cartridge 70.

Figure 11:
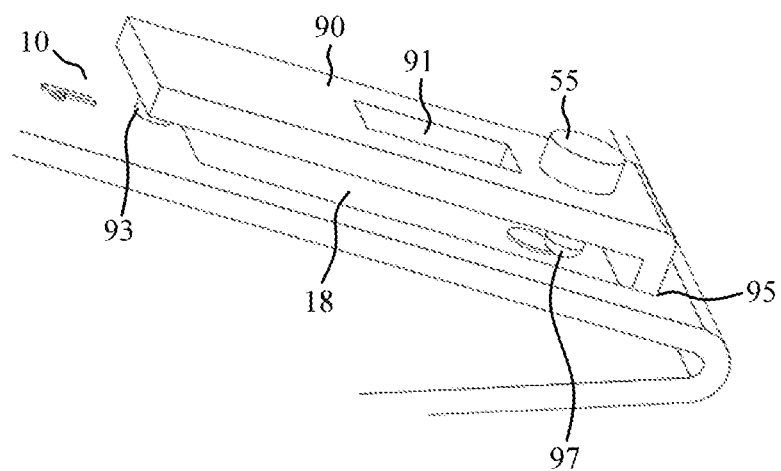
FIG. 11 is a view illustrating a configuration of a clamp (90) in the embodiment illustrated in FIG. 10.

According to an additional aspect, the heating unit 55 may be a non-contact type infrared heater. As illustrated in FIGS. 10 to 12, the infrared heater 55 is installed above the clamp 90 to face the cartridge 70.

Figure 13:
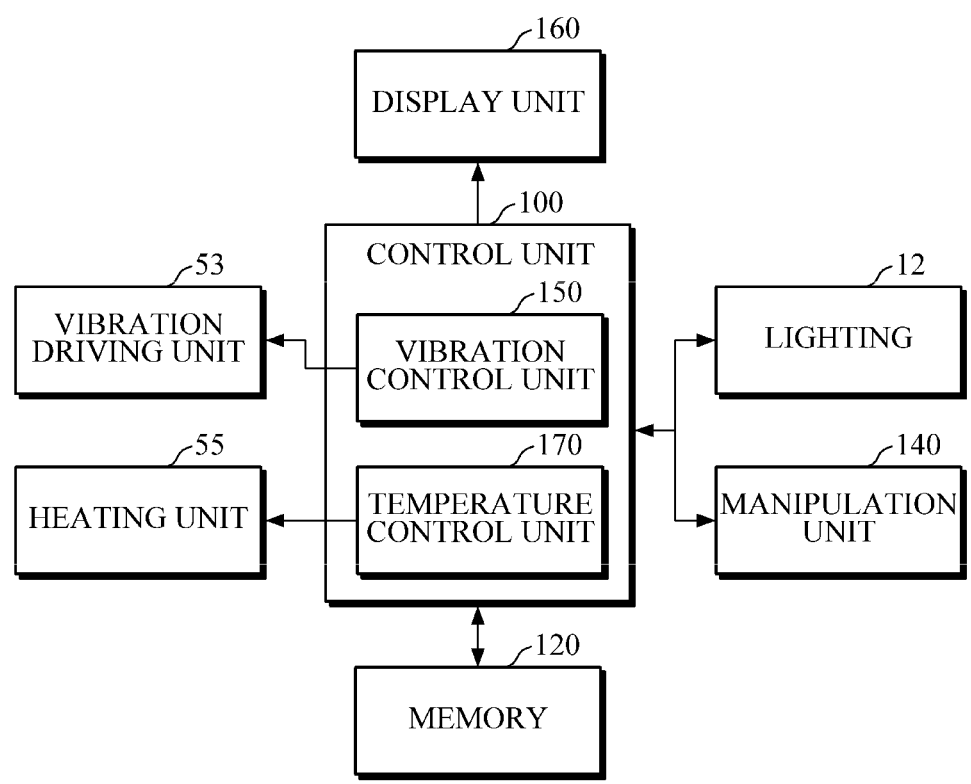
FIG. 13 is a block diagram illustrating a functional configuration of the lateral flow diagnostic testing apparatus according to one embodiment of the proposed invention.

FIG. 13 is a block diagram illustrating a functional configuration of the lateral flow diagnostic testing apparatus according to one embodiment of the proposed invention. In the embodiment illustrated in FIG. 13, the control unit 100 is implemented on a substrate fixed to the bottom of the measurement assembly 10. In the embodiment illustrated in FIG. 13, a configuration of the vibration control unit 150 and the temperature control unit 170 illustrated as a configuration of the control unit 100 may be implemented as a program command set executed by a microprocessor. The program commands may be stored and executed in the memory 120. The memory 120 may include one memory element or a plurality of different types of memory elements.

Referring to FIG. 13, in one embodiment, a manipulation unit 140 is implemented as a key button and includes a measurement start button to start a measurement process for each cartridge 70. The display unit 160 displays user interface information and the like for guiding an operational state and an operation of the device.

When a power source is turned on, the control unit 100 checks whether the measurement start button is pressed. When it is detected that the measurement start button is pressed for one among four cartridges, the vibration driving unit 53 is driven in one direction or the plurality of directions preset through a vibration control unit 150, and a heating unit 55 is driven to heat at a preset optimal temperature through a temperature control unit 170. A diagnosis result may be checked by visually checking a test line and a control line through an observation window. In this case, lighting 12 inside the observation window is turned on to aid in checking of the user.

According to the proposed invention, reactivity in a lateral flow diagnostic testing kit apparatus can be increased to reduce a time taken for measuring. In addition, sensitivity can be improved by facilitating coupling between materials including a specimen and antibodies which affect coupling and an antibody reaction.

What is claimed is:

1. A lateral flow diagnostic testing apparatus comprising:
    a main body housing; and
    a measurement assembly in which a cartridge is loaded and which is inclined with respect to the main body housing in a lateral flow direction of the cartridge,
    wherein the main body housing and the measurement assembly are rotatably hinge-coupled by a hinge unit.

2. The lateral flow diagnostic testing apparatus of claim 1, further comprising:
    an inclination driving unit which is coupled to the hinge unit to rotatably drive the measurement assembly with respect to the main body housing; and
    a control unit including an inclination control unit which controls rotational driving of the inclination driving unit to adjust inclination of the measurement assembly with respect to the main body housing.

3. The lateral flow diagnostic testing apparatus of claim 1, wherein the measurement assembly includes a tray including an accommodation groove in which the cartridge is loaded and slidably withdrawn to load the cartridge.

4. The lateral flow diagnostic testing apparatus of claim 3, wherein:
    the measurement assembly further includes an optical sensor fixed above the tray; and
    the lateral flow diagnostic testing apparatus further includes a control unit including an analysis unit configured to analyze a signal input from the optical sensor to determine a color development of the cartridge and process a diagnosis.

5. The lateral flow diagnostic testing apparatus of claim 1, wherein the measurement assembly further includes a vibration driving unit disposed on a loading surface on which the cartridge is loaded.

6. The lateral flow diagnostic testing apparatus of claim 5, wherein the vibration driving unit includes:
    an X-axis vibration unit configured to vibrate the cartridge in a longitudinal direction;
    a Y-axis vibration unit configured to vibrate the cartridge in a width direction; and
    a Z-axis vibration unit configured to vibrate the cartridge in a thickness direction.

7. The lateral flow diagnostic testing apparatus of claim 6, wherein the Z-axis vibration unit includes an oscillator tip which is exposed to be in direct contact with the cartridge through a hole in a bottom of a loading surface on which the cartridge is loaded.

8. The lateral flow diagnostic testing apparatus of claim 1, further comprising a heating unit fixed to the measurement assembly to face the cartridge.

9. The lateral flow diagnostic testing apparatus of claim 8, wherein the heating unit includes an infrared heater installed in the measurement assembly to face the cartridge from above the cartridge.

10. The lateral flow diagnostic testing apparatus of claim 5, wherein the measurement assembly further includes a clamp which presses and pressurizes the loaded cartridge from above.

11. The lateral flow diagnostic testing apparatus of claim 10, wherein the measurement assembly further includes an infrared heater installed on the clamp to be disposed to face the cartridge loaded under the infrared heater.

12. The lateral flow diagnostic testing apparatus of claim 6,
    further comprises a tray driving unit configured to withdraw and return the tray along a tray rail,
    wherein the X-axis vibration unit, the Y-axis vibration unit, and the Z-axis vibration unit are driven in a manner that obtains vibration by moving the tray driving unit back and forth.

\* \* \* \* \*